United States Patent
Huang et al.

(10) Patent No.: US 8,513,620 B2
(45) Date of Patent: Aug. 20, 2013

(54) AUXILIARY STAGE AND METHOD OF UTILIZING AUXILIARY STAGE

(75) Inventors: Lang-Yu Huang, Hsinchu County (TW); Yu-Sen Wang, Taipei (TW)

(73) Assignee: Inotera Memories, Inc., Hwa-Ya Technology Park Kueishan, Taoyuan (TW)

( * ) Notice: Subject to any disclaimer, the term of this patent is extended or adjusted under 35 U.S.C. 154(b) by 331 days.

(21) Appl. No.: 12/902,165

(22) Filed: Oct. 12, 2010

(65) Prior Publication Data
US 2011/0260056 A1 Oct. 27, 2011

(30) Foreign Application Priority Data
Apr. 27, 2010 (TW) ................. 99113250 A

(51) Int. Cl.
*H01J 37/20* (2006.01)
(52) U.S. Cl.
CPC ..................................... *H01J 37/20* (2013.01)
USPC ........................ 250/440.11; 250/310; 250/311
(58) Field of Classification Search
USPC ................... 250/304, 307, 310, 311, 440.11, 250/442.11
See application file for complete search history.

(56) References Cited

U.S. PATENT DOCUMENTS

| | | | |
|---|---|---|---|
| 6,538,254 B1 * | 3/2003 | Tomimatsu et al. | 250/442.11 |
| 6,717,156 B2 * | 4/2004 | Sugaya et al. | 250/440.11 |
| 6,768,110 B2 * | 7/2004 | Alani | 250/307 |
| 7,053,383 B2 * | 5/2006 | Moore | 250/440.11 |
| 7,525,108 B2 | 4/2009 | Tomimatsu | |
| 7,759,656 B1 * | 7/2010 | Walck et al. | 250/440.11 |
| 8,288,737 B1 * | 10/2012 | Walck | 250/440.11 |
| 2008/0312726 A1 | 12/2008 | Frank | |

FOREIGN PATENT DOCUMENTS
TW 200919578 5/2009

* cited by examiner

*Primary Examiner* — Jack Berman
(74) *Attorney, Agent, or Firm* — Winston Hsu; Scott Margo

(57) ABSTRACT

An auxiliary stage for holding an electron microscope specimen includes a bottom part and a supporting part. The bottom part includes a first top surface, and the supporting part includes a second top surface and a side surface. The supporting part is fixed on the first top surface, and the side surface of the supporting part is substantially perpendicular to the first top surface of the bottom part. Therefore, the auxiliary stage is in a shape of a reversed T. A slit is embedded in the second top surface of the supporting part. A specimen holder is mounted in the slit, and a specimen is fixed on the specimen holder.

14 Claims, 5 Drawing Sheets

AUXILIARY STAGE AND METHOD OF UTILIZING AUXILIARY STAGE

BACKGROUND OF THE INVENTION

1. Field of the Invention

The invention relates to an auxiliary stage for preparing an electron microscope specimen and a method of utilizing the auxiliary stage.

2. Description of the Prior Art

In the semiconductor fabricating process, some small particles and defects are unavoidable. As the size of devices shrinks and the integration of circuits increases gradually, those small particles or defects affect the properties of the integrated circuits more seriously. In order to improve the reliability of semiconductor devices, a plurality of tests and monitors is performed continuously to find the root cause of the defects or particles. Then, process parameters can be tuned correspondingly to reduce a presence of defects or particles so as to improve the yield and reliability of the semiconductor fabricating process.

The scanning transmission electron microscope (STEM) is a combination of transmission electron microscope (TEM) and scanning electron microscope (SEM) in one instrument, which is a very important instrument used in material analysis.

Generally speaking, the optimum thickness of an STEM specimen needs to be smaller than 0.1 μm. Therefore, the specimen needs to be thinned by a focus ion beam (FIB) tool for reaching the optimum thickness. Before using the focus ion beam, a layer of platinum is coated on the specimen by a platinum sputter to increase the specimen conductivity and the surface resolution. However, since the traditional platinum sputter uses clay as a specimen stage, the solvent in the clay will pollute the chamber of the platinum sputter during the sputtering.

Moreover, when the STEM specimen is bombarded by electrons for a period of time, carbon may accumulate on the surface of the specimen, and the resolution will decrease. Therefore, a plasma cleaner is used to clean carbon accumulated on the specimen. However, the current plasma cleaner is only designed for TEM specimens. A STEM specimen can not fixed in the chamber of the plasma cleaner properly.

Therefore, a novel stage is needed to hold the STEM specimen during the specimen preparation process such as platinum sputtering, removing amorphous silicon or removing carbon.

SUMMARY OF THE INVENTION

It is one objective of the present invention to provide an auxiliary stage to cope with numerous specimen preparation processes for STEM specimens.

According to a preferred embodiment of the present invention, an auxiliary stage includes: a bottom part having a first top surface and a supporting part having a second top surface and a side surface, wherein the supporting part is fixed on the first top surface, and the side surface of the supporting part is substantially perpendicular to the first top surface of the bottom part, wherein a slit is disposed in the second top surface of the supporting part, a specimen holder is mounted in the slit, and a specimen is fixed on the specimen holder.

According to another preferred embodiment of the present invention, a method of utilizing an auxiliary stage is performed by using a specimen preparation tool, and the specimen preparation tool includes a chamber. The method comprises: first an auxiliary stage comprising a bottom part and a supporting part is provided. Then, a specimen holder is fixed in a slit on the supporting part, and a specimen is fixed on the specimen holder. Then, the auxiliary stage, the specimen holder and the specimen are disposed into the chamber. Later, the specimen preparation tool is turned on to cope with the specimen. Finally, the specimen holder is removed along with the specimen from the auxiliary stage.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
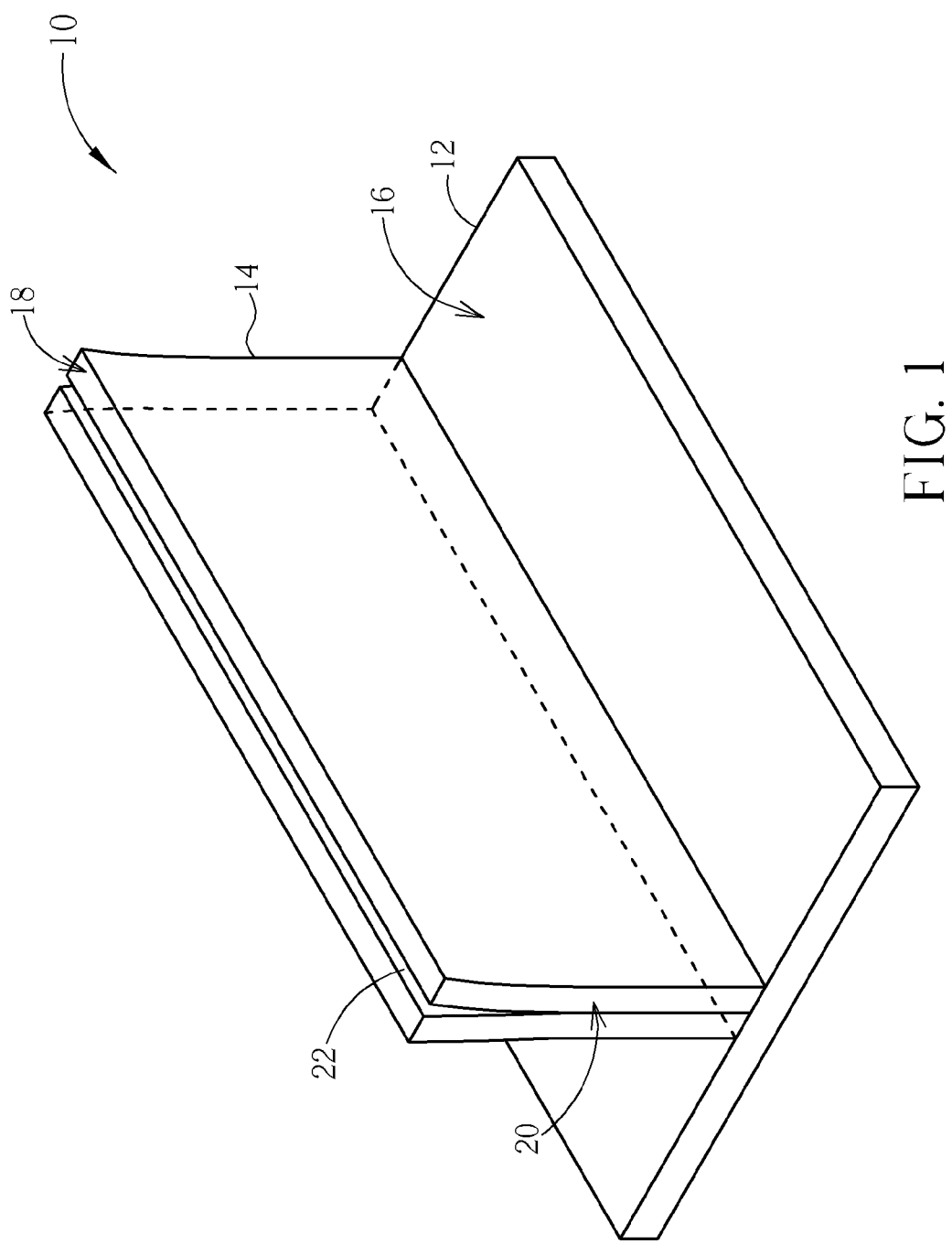
FIG. 1 depicts an auxiliary stage schematically according to a preferred embodiment of the present invention.
Figure 2:
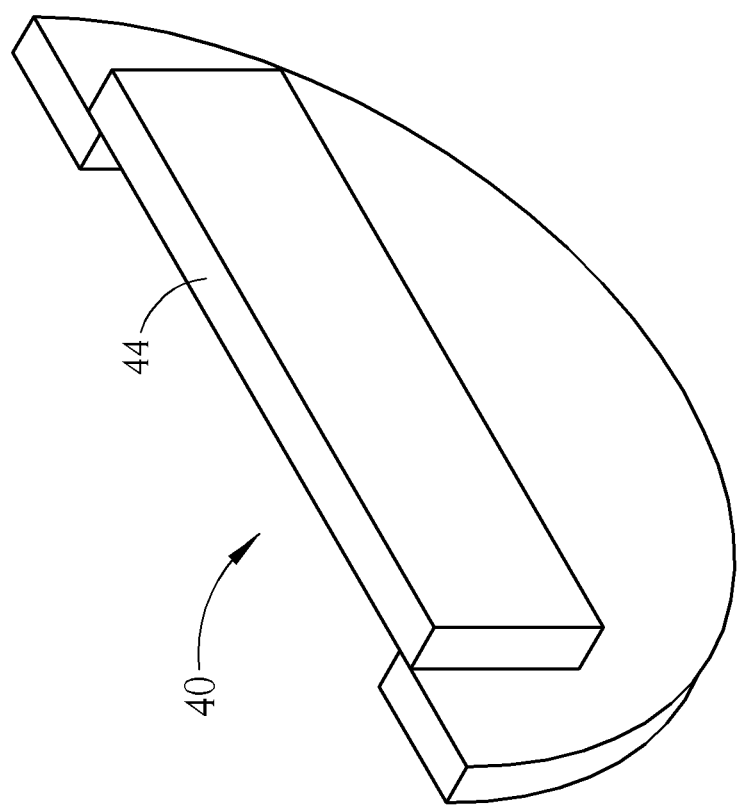
FIG. 2 depicts a specimen holder with a specimen thereon schematically according to a preferred embodiment of the present invention.

FIG. 1 depicts an auxiliary stage schematically according to a preferred embodiment of the present invention. FIG. 2 depicts a specimen holder with a specimen schematically according to a preferred embodiment of the present invention.

As shown in FIG. 1, an auxiliary stage 10 includes a bottom part 12 and a supporting part 14. The bottom part 12 includes a top surface 16, and the supporting part 14 includes a top surface 18 and a side surface 20. The supporting part 14 is fixed on the top surface 18 of the bottom part 12. The auxiliary stage 10 is in a shape of a reversed T. The side surface 20 of the supporting part 14 is substantially perpendicular to the top surface 16 of the bottom part 12, thus the auxiliary stage 10 is in a shape of a reversed T. Furthermore, a slit 22 is embedded into the top surface 18 of the supporting part 14. Please refer to FIG. 2. The slit 22 is for fixing a specimen holder 40. According to a preferred embodiment of the present invention, the auxiliary stage 10 including the bottom part 12 and the supporting part 14 can be made of at least one silicon-containing material. For example, the auxiliary stage 10 can be made by a discarded wafer. The method of making the auxiliary stage will be introduced afterwards.

As shown in FIG. 2, the specimen holder 40 is used for fixing a specimen 44. Generally speaking, the specimen holder 40 can be a half copper ring used for holding the specimen 44 while TEM or STEM photos are taken. Besides the function of holding the specimen 44 while TEM or STEM photos are taken, the specimen holder 40 can be engaged with the auxiliary stage 10 when performing a specimen preparation process. The specimen 44 may be an electron microscope specimen, such as an SEM specimen or a TEM specimen. For example, the specimen 44 can be a specimen after an FIB process that is going to remove an amorphous layer thereon. Alternatively, the specimen 44 can be a specimen which is going to be coated with platinum. Or the specimen 44 can be a specimen with carbon buildup after the TEM or STEM analysis.

Figure 3:
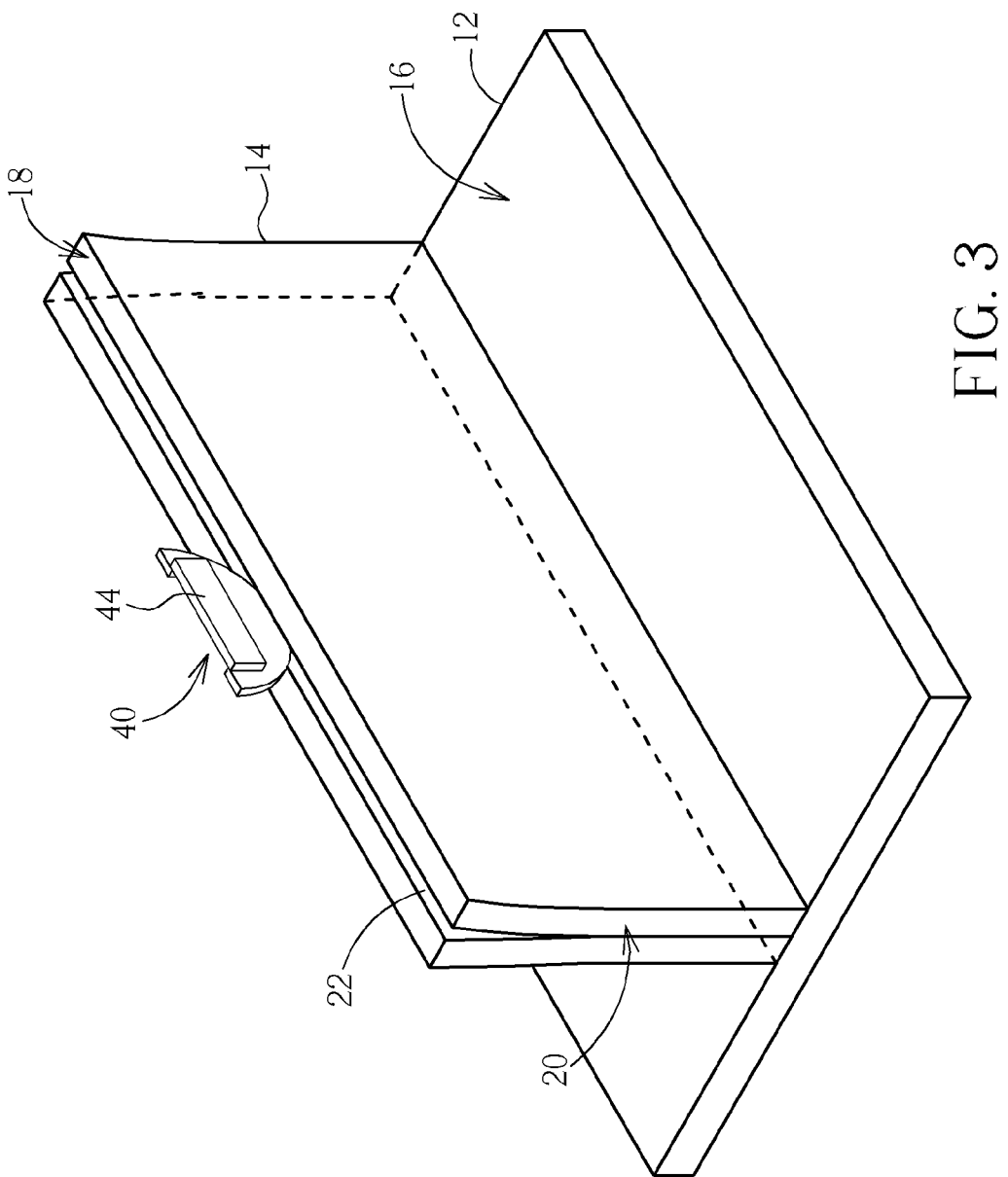
FIG. 3 depicts an assembling of a specimen holder and an auxiliary stage schematically.

FIG. 3 depicts an assembling of the specimen holder 40 and the auxiliary stage 10 schematically. As shown in FIG. 3, the specimen holder 40 is fixed in the slit 22 of the auxiliary stage 10. Furthermore, based on different requirements, more than one specimen holder 40 can be fixed in the slit 22.

Figure 4:
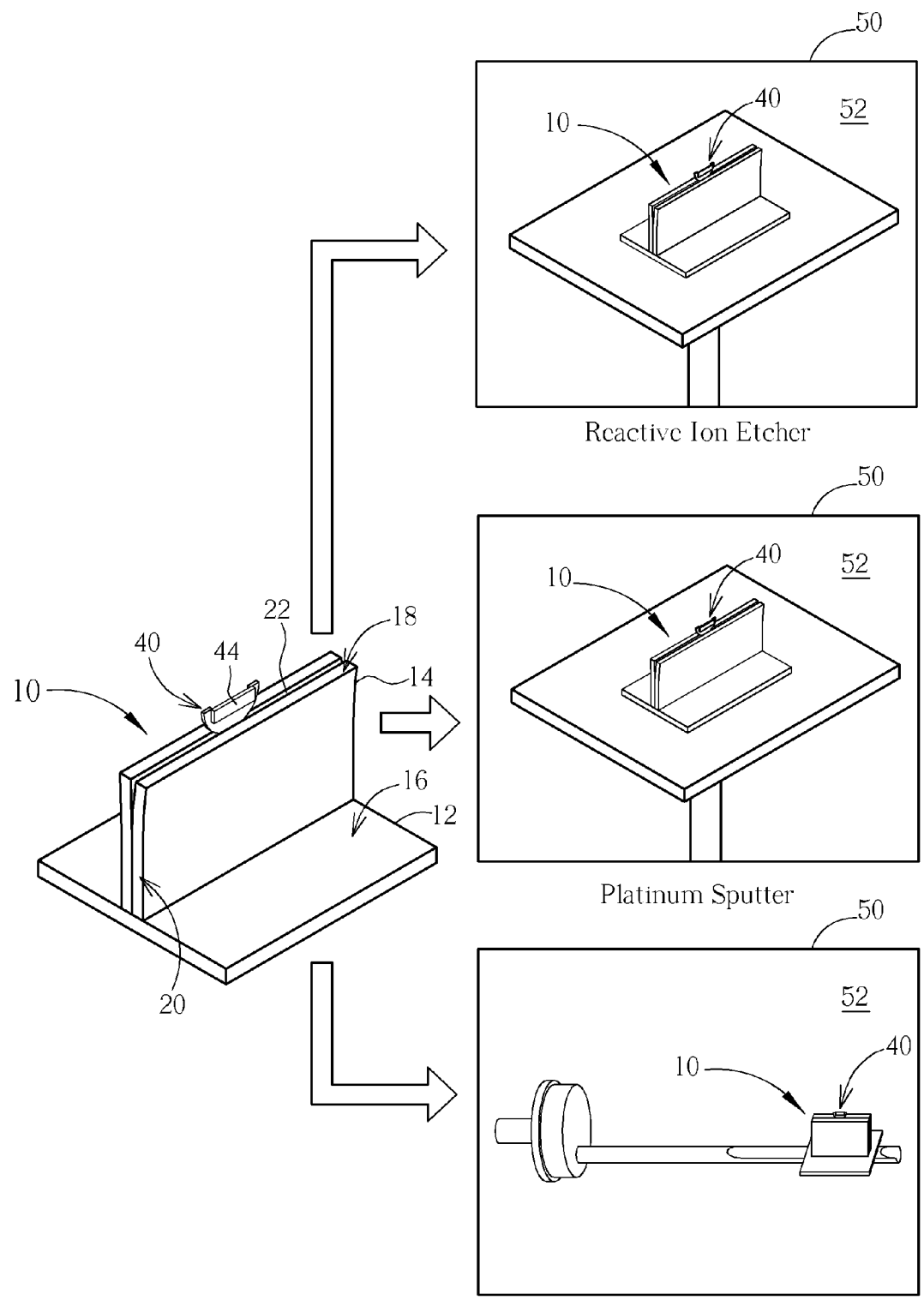
FIG. 4 depicts the method of utilizing an auxiliary stage according to a preferred embodiment of the present invention.

FIG. 4 depicts a method of utilizing an auxiliary stage according to a preferred embodiment of the present invention. Please refer to FIGS. 3 and 4, after the specimen 44 along with the specimen holder 40 are fixed on the auxiliary stage 10. The specimen 44 can be sent into a chamber 52 of a specimen preparation tool 50 to perform a specimen preparation process. The specimen preparation process may be a process of removing the amorphous silicon on the specimen 44, a process of removing carbon on the specimen 44, or a process of coating platinum on the specimen 44. The specimen preparation tool 50 may be a reactive ion etcher (RIE) for cleaning the amorphous silicon on the surface of the specimen 44, a plasma cleaner for removing the carbon on the specimen 44, or a platinum sputter for coating platinum on the specimen 44. According to a preferred embodiment of the present invention, if the specimen preparation tool 50 is a platinum sputter, the specimen 44 after sputtering will be removed from the auxiliary stage 10 along with the specimen holder 40. Then, the specimen 44 and the specimen holder 40 will be put into a FIB tool for thinning the specimen 44. According to another preferred embodiment of the present invention, if the specimen preparation tool 50 is a RIE, the specimen 44 after being etched will be removed from the auxiliary stage 10 along with the specimen holder 40. Later, the specimen 44 and the specimen holder 40 will be put into a chamber of an electron microscope to take photos. According to another preferred embodiment of the present invention, if the specimen preparation tool 50 is a plasma cleaner, the specimen 44 cleaned in the plasma cleaner will be removed from the auxiliary stage 10 along with the specimen holder 40. Subsequently, the specimen 44 and the specimen holder 40 will be put back into a chamber of an electron microscope to continue taking photos. The electron microscope can be an SEM or a TEM. It is note worthy that the auxiliary stage 10 is only used at the specimen preparation process. When taking the electron microscope photos, the auxiliary stage 10 is not in the chamber of the electron microscope.

Figure 5:
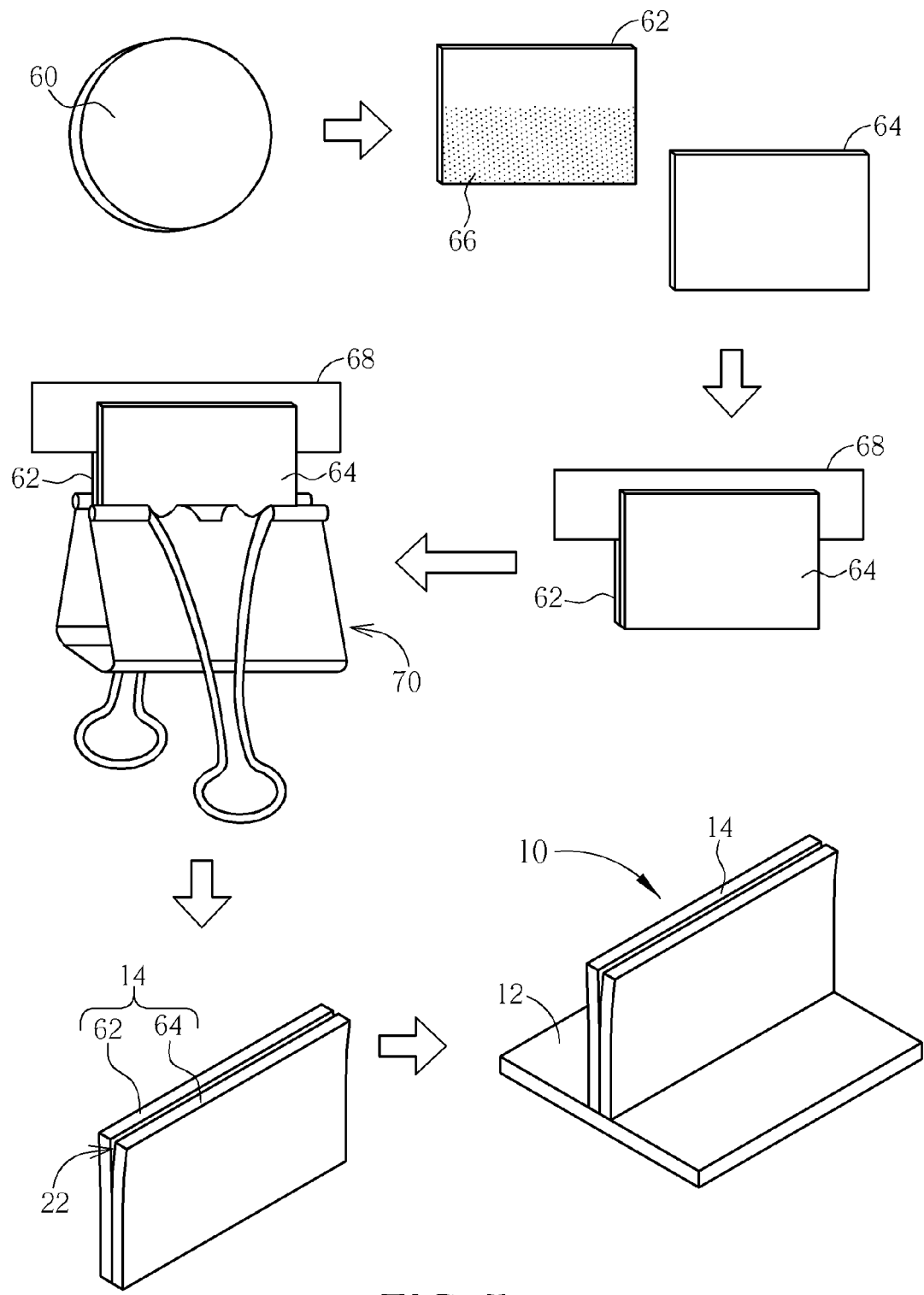
FIG. 5 depicts a method of fabricating an auxiliary stage of the present invention.

FIG. 5 depicts a method of fabricating an auxiliary stage of the present invention. As shown in FIG. 5, first, a discarded wafer 60 is cut into two rectangular structures 62, 64. Next, an adhesion 66 is coated on a region of the surface of the rectangular structure 62. Then, a disposable supporter 68 such as a paper is disposed at another region of the surface of the rectangular structure 62. The region which the disposable supporter 68 disposed on is not coated with the adhesion 66. The disposable supporter 68 is for making a slit between the rectangular structures 62, 64. Later, the rectangular structure 64 overlaps on the rectangular structures 62. After that, a fixer 70 such as a clip, clips the rectangular structures 62, 64 together. Subsequently, the rectangular structures 62, 64, the fixer 70, and the disposable supporter 68 are heated up for half an hour to fix the relative position of the rectangular structures 62, 64. Please refer to both FIG. 1 and FIG. 5. Then, the disposable supporter 68 is removed and the rectangular structures 62, 64 form the supporting part 14. The position where the disposable supporter 68 was original disposed forms a slit. Next, the bottom 12 is formed by another discarded wafer (not shown) by cutting the discarded wafer into another rectangular structure. Then, the supporting part 14 is fixed on the bottom 12 by the adhesion 66 to form a reversed T. Now the auxiliary stage 10 of the present invention is completed. Although the auxiliary stage 10 is formed by numerous rectangular structures in FIG. 5, the discarded wafer 60 can be cut into other geometric structures such as circles or polygons, and the geometric structures can be combined by the method described in FIG. 5.

Conventionally, the RIE does not have any stage for holding STEM or TEM specimens. The auxiliary stage of the present invention can be used for holding the half copper ring and the specimen. So the amorphous silicon on the specimen can be removed by the RIE. Moreover, the auxiliary stage of the present invention can be used in the plasma cleaner for fixing the half copper ring and the specimen in the chamber of the plasma cleaner. Furthermore, the auxiliary stage of the present invention can replace the clay used in the platinum sputter so the solvent in the clay will not pollute the chamber. The auxiliary stage of the present invention can provide environmental protection and save costs because the auxiliary stage can be made of discarded wafers.

Those skilled in the art will readily observe that numerous modifications and alterations of the device and method may be made while retaining the teachings of the invention.

What is claimed is:

1. An auxiliary stage, comprising:
    a bottom part having a first top surface; and
    a supporting part having a second top surface and a side surface, the supporting part fixed on the first top surface with an adhesive layer, and the side surface of the supporting part being substantially perpendicular to the first top surface of the bottom part, wherein a slit is disposed in the second top surface of the supporting part, a specimen holder is mounted in the slit, and a specimen is fixed on the specimen holder.

2. The auxiliary stage of claim 1, wherein the bottom part and the supporting part are made of a silicon containing-material.

3. The auxiliary stage of claim 1, wherein the supporting part comprises a first rectangular structure and a second rectangular structure, the first rectangular structure and the second rectangular structure are fixed together.

4. The auxiliary stage of claim 3, wherein the slit is disposed between the first rectangular structure and the second rectangular structure.

5. The auxiliary stage of claim 1, wherein the specimen holder is a half copper ring.

6. A method of utilizing an auxiliary stage, the method is performed by using a specimen preparation tool, the specimen preparation tool comprising a chamber, wherein the method comprises:
    providing an auxiliary stage according to claim 1;
    fixing a specimen holder in a slit on the supporting part, wherein a specimen is fixed on the specimen holder;
    disposing the auxiliary stage, the specimen holder and the specimen into the chamber;
    turning on the specimen preparation tool to cope with the specimen; and
    removing the specimen holder along with the specimen from the auxiliary stage.

7. The method of utilizing an auxiliary stage of claim 6, wherein the bottom part comprises a first top surface and the supporting part comprises a second top surface and a side surface.

8. The method of utilizing an auxiliary stage of claim 7, wherein the supporting part is fixed on the first top surface, and the side surface of the supporting part is substantially perpendicular to the first top surface of the bottom part, and the slit is embedded in the second top surface.

9. The method of utilizing an auxiliary stage of claim 6, wherein the auxiliary stage is made of a silicon containing-material.

10. The method of utilizing an auxiliary stage of claim 6, wherein the specimen preparation tool comprises a reactive ion etcher, a plasma cleaner, or a platinum sputter.

11. The method of utilizing an auxiliary stage of claim 6, wherein the specimen is an electron microscope specimen.

12. The method of utilizing an auxiliary stage of claim 11, wherein the specimen comprises an SEM specimen or a TEM specimen.

13. The method of utilizing an auxiliary stage of claim 6, wherein the specimen holder is a half copper ring.

14. The method of utilizing an auxiliary stage of claim 6, further comprising after the specimen holder along with the specimen are removed from the auxiliary stage, the specimen holder and the specimen being disposed into a chamber of an electron microscope.

* * * * *